United States Patent [19]

Kim et al.

[11] Patent Number: 4,722,336

[45] Date of Patent: Feb. 2, 1988

[54] PLACEMENT GUIDE

[76] Inventors: Michael Kim; Chong C. Kim, both of 3563 Twinlake Ridge Dr., Westlake Village, Calif. 91361

[21] Appl. No.: 695,161

[22] Filed: Jan. 25, 1985

[51] Int. Cl.$^4$ ............................................. A61B 17/00
[52] U.S. Cl. .................................. 128/303 B; 378/162
[58] Field of Search ..................... 128/303 B; 269/322, 269/328; 378/162-164, 205

[56] References Cited

U.S. PATENT DOCUMENTS

4,058,114 11/1977 Soldner ............................ 128/303 B
4,602,622 7/1986 Bär et al. .......................... 128/303 B

*Primary Examiner*—Richard J. Apley
*Assistant Examiner*—H. Macey

[57] ABSTRACT

A guide for locating a target object within a visually opaque but x-ray transparent object has a base creating a first reference plane. A vertical post extends upward from the base perpendicular to the first reference plane. First target sighting members, which are at least partially opaque to x-ray are mounted for movement relative to the vertical support member and provide for creating a line parallel to the reference plane through the target. A system is provided for aligning x-ray fluoroscope with the first target. A second target has two target sighting members, one on an arm above the target object and the other on an arm below the target object. The x-ray fluoroscope is aligned with these such that when the x-ray fluoroscope is projecting in a line parallel to the upright support and perpendicular to the reference plane, it extends through opaque sights and through the target. The distance from the second target to the upright support is measured, and the probe is mounted at a predetermined angle, the line of which extends through a point on the vertical post equal to the distance from the post to the second sight divided by the tangent of the predetermined angle.

10 Claims, 19 Drawing Figures

PLACEMENT GUIDE

BACKGROUND OF THE INVENTION

1. Field of the Invention:

The present invention is a method and device (1) to determine precisely the three-dimensional coordinates of a target located internally within a visibly opaque but x-ray discernible object (e.g. a surgical patient) using x-ray fluoroscope imaging and (2) to use the determined coordinates to define a guiding path to reach the target location. The invention is useful in needle and drill placement for medical/surgical application such as highly localized chemical injection, biopsy, and orthopaedic procedures involving the bone. The specific use described relates a guide for correct positioning of a needle into the space adjacent a ruptured vertebrae disk for chemonucleolysis.

2. The Prior Art:

Chemonucleolysis is a method of healing ruptured vertebrae disks in which a surgeon injects chymopapain enzyme into the disk space. It is believed that the enzyme dissolves nucleus mucoproteins, which aids in healing ruptured vertebrae disks. Smith, U.S. Pat. No. 3,320,131 (1967) discloses in general terms the use of injected chymopapain for treating herniated intervertebral disks.

Typically, a surgeon makes an opening in the skin and attempts to position the probe properly and at the correct angle such that it contacts the disk to be treated. Some prior art guides, which are discussed below, have been used, but the positioning of the probe is frequently a manual operation. Once the probe is correctly positioned, a precise amount of chymopapain or other dissolving enzyme is injected through the probe into the desired location. The probe is usually positioned under a fluoroscope so that the surgeon can determine the location of the probe. He or she is given little leeway because the relatively strong muscles in the back limit movement of the probe once it is inserted through muscle tissue. Therefore, if the probe does not reach its desired location, it must be removed substantially from below the skin, and it must be reinserted at a new opening. Some very skilled and experienced surgeons can cause the probe to change directions below the skin and to locate the treatment site easily, but only one who is expert in this field has the required practice and skill.

As with any surgical procedure, there are risks. The principal one in chemonucleolysis is having the probe reach and thus damage the spinal cord or nerves exiting from the spinal cord between the vertebrae.

Workers designing surgical instruments have recognized that a device for positioning the needle guide in chemonucleolysis would be advantageous. Froning, U.S. Pat. No. 3,941,127 (1976) teaches a needle guide in which the device is taped to the patient and two vertical supports hang down along the patient's back. A chain hangs vertically downward from an arm attached to an assembly extending between the horizontal supports. The chain is positioned to be in line with a disk space between adjacent vertebrae into which the chymopapain is to be injected. A needle guide support is aligned with the chain and extends upward from a horizontal member also held by the vertical supports and carries a needle guide mounted at a 45° angle to vertical. The needle guide can have one of a number of different sleeves to move up or down on the upward support, and the size of the sleeve is chosen in a procedure that takes place before the actual surgery. The bottom of the sleeve is aligned with an x-ray marker at the center of the spine. The distance from the bottom of the sleeve to the needle and from the sleeve inward to the center of the spine should be equal. This unit suffers because it is attached to the patient, which requires taping and leveling. For accurate distance and angle of entry, the x, y and z axes must be fixed. By using the patient as a reference surface, it is difficult for Froning to set reference axes. It also does not readily determine the horizontal distance to the midsaggital plane. Froning, U.S. Pat. No. 3,964,480 (1976) adds indexing to the sleeve and to the angled needle guide for calculating the location to insert the probe beneath the skin, but some of the aforementioned drawbacks still exist.

There are other devices used to locate a part of a surgical instrument to an area below the skin. Examples of some of these systems include Volkman, U.S. Pat. No. 3,115,140 (1963), Stenvall, U.S. Pat. No. 3,016,899 (1962), Barbier, U.S. Pat. No. 4,360,028 (1982) and Zukowski, U.S. Pat. No. 4,390,018, (1983), which is particularly directed to spinal procedures. In addition, Froning, U.S. Pat. No. 3,875,595 (1975) also relates to intervertebral disk prosthesis.

It is an object of the present invention to disclose and provide a method and apparatus for locating a target object within a visually opaque but x-ray transparent object using a fluoroscope and to determine a proper path that a needle, probe or drill takes to reach the target object. A narrow object primarily for chemonucleolysis, but the one described with reference to the exemplary embodiment is to locate the disk space (target object) in the patient (opaque object) and to determine the correct angle for the needle to reach the disk space.

Another object of the present invention is to disclose and provide a device that is free standing and does not have to be attached to the object (e.g. patient) in which the target object is located. Another object is to disclose and provide a device that will locate the needle guide at the proper location beneath the skin in a combined, easily performed operation in which the same device can be used to measure the horizontal distance from the device to the midsaggital plane, which distance is needed for proper positioning of the needle and probe support.

These and other objects of the present invention will be evident from the more detailed description of the invention.

SUMMARY OF THE INVENTION

The guide for locating a target object within a visually opaque but x-ray transparent object of the present invention includes a base for creating a first reference plane. In surgery, the base is positioned on a surgical table under the patient. A first support member is attached to the base and extends perpendicular, normally upward, to the first reference plane. First and second target sighting members, which are at least partially opaque to x-ray, are mounted for movement relative to the first support member. The first target sighting member is moveable along the first support such that it and the axis of projection of an x-ray generator and receiver and the target object are in a first reference line, which is parallel to the first reference plane. The second target sighting member is positioned relative to the first support on a arm that is perpendicular to the first support, and the second target sighting member is positioned along the arm. The axis of projection of an x-ray generator and receiver through the second target sighting member and the target object creates a second reference line, which is perpendicular to the first reference plane. A probe support is positioned along the first support member at a predetermined angle to the first support member at a distance above the first reference line equal to the distance from the first support member to the second reference line divided by the tangent of the predetermined angle. The probe support allows the probe, which will reach the target object, to move along the predetermined angle to reach the target object.

In the particular device used in chemonucleolysis, the preferred angle of entry for most vertebrae is 45°. Therefore, the guide supporting the needle, which passes through the patient's back muscles and reaches the damaged disk, is mounted at a 45° angle to the first, normally vertical, support. Tan 45° = 1. If the guide path is at 45°, the path passes through a point on the first support equidistant from the first reference line and from the second reference line.

A pair of opaque, perpendicular cross hairs may be attached to the front of the x-ray detector to be imaged on the fluoroscope screen that the surgeon views. The manner in which they are mounted on the x-ray detector permits them to be rotated so that they can be aligned with the spine. When the needle is inserted through the back muscles, the surgeon may keep the needle aligned with one of the cross hairs. If the needle becomes visible in the fluoroscope image, the surgeon will know that it is misaligned.

BRIEF DESCRIPTION DESCRIPTION OF THE DRAWINGS

FIG. 6 relates to the first target sighting members, and FIG. 7 shows details of an arm which holds the second target sighting member.

FIG. 12 is similar to orientation to FIG. 10 and shows much of the modified probe support of this embodiment. FIGS. 13 and 14 are both taken through plane 13—13 in FIG. 12. FIG. 13 shows the probe support in its closed position, and FIG. 14 shows the probe support in its open position.

FIGS. 18 and 19 (sheet 7) are schematic views designed to show the geometry of the operation of the probe device of the present invention. FIG. 18 is a side elevation, and FIG. 19 is a plan view.

DETAILED DESCRIPTION OF THE PREFERRED EMBODIMENT

Figure 1:
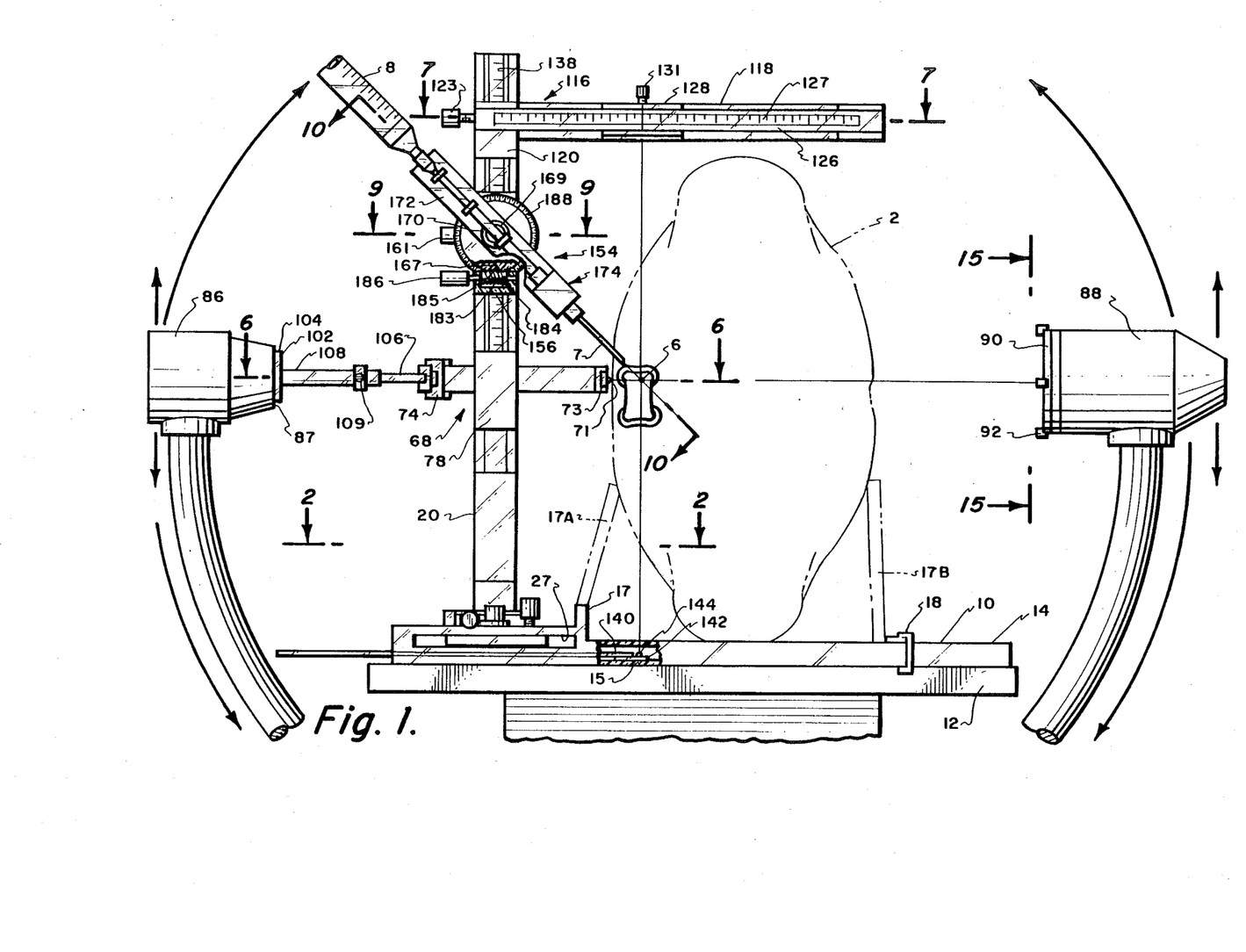
FIG. 1 (sheet 1) is a side elevation, partially cut away of the guide of the present invention.
Figure 18:
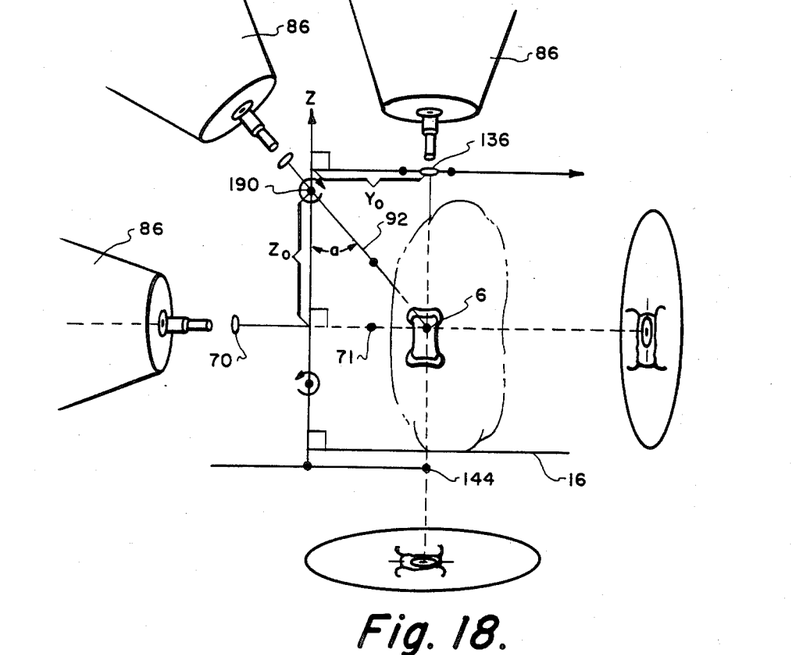

The present invention determines precisely three-dimensional Cartesian coordinates of a target object located within a visibly opaque but x-ray transparent object. The exemplary embodiment is designed for locating a precise disk space (the target object) in the patient (the opaque object). It includes base means for creating a first reference plane positioned under the patient. In the exemplary embodiment, bottom surface 15 of base 10 (FIGS. 1 and 2) rests on a surgical table 12 (FIG. 1). Base 10 is formed of plastic and is transparent to x-rays. A patient 2 lies on his side facing to the right (FIG. 1) on top surface 14 of base 10. Top surface 14 of base 10 (FIG. 1 and 2), which is parallel to bottom surface 15, defines a first reference plane 16 (FIG. 18). Reference plane 16 is occasionally referred to as the "horizontal" or X-Y plane. See FIG. 19. Base 10 is designed to create its own reference plane irrespective of whether surgical table 12 or the floor on which the table rests is actually horizontal. Because first reference plane 16 is close to horizontal, it is called that.

Figure 19:
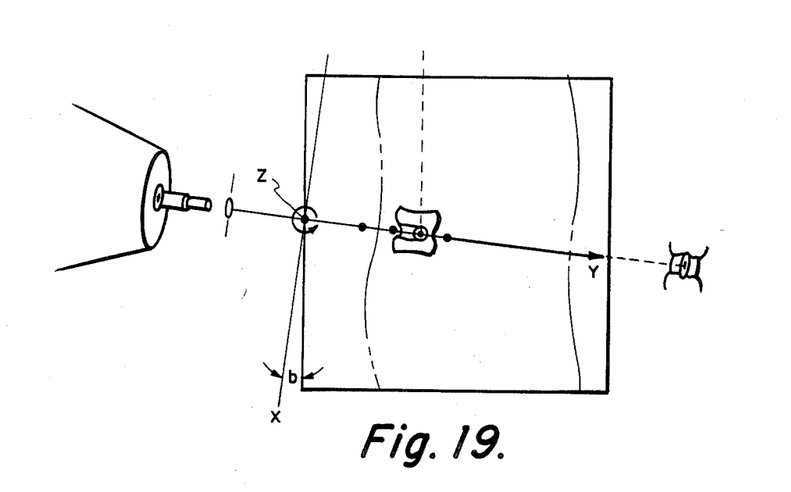

Base 10 is moveable for rough measurements to translate in the x-y plane (FIG. 19). This movement takes place by raising the patient somewhat. A short vertical wall 17 (FIG. 1) may separate the area supporting the patient (right side of FIG. 1) from the rest of the base. Vertical wall 17 may be extended upward at 17A in phantom in FIG. 1 to assist in holding the patient immoveable. If the patient moves during any step, the method must be restarted. A second wall 17B may be clamped to base 10 by clamps 18 on the other side of the patient to act as a vice-like support for immobilizing the patient.

Figure 7:
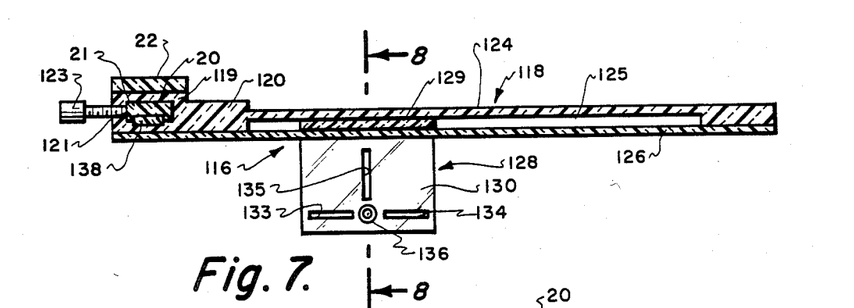
Figure 8:
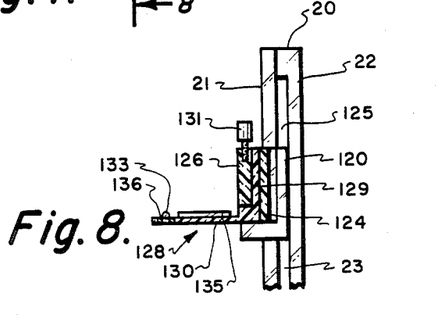
FIG. 8 (sheet 3) is a sectional view of the second target sighting member of the present invention taken through plane 8—8 of FIG. 7.

A first support member is attached to the base and extends perpendicular to first reference plane 16. First support member 20 (FIGS. 1, 2, 4, 5, 6, 7, 9, and 10) is attached to base 10. Sometimes called the upright or vertical support, it consists of a front post 21 and rear post 22 separated by vertical space 23 (FIG. 8). The two post/slot arrangement is not needed in the lower portion of support 20. Therefor, it is a solid member.

The connection between first support member 20 and base 10 in the exemplary embodiment provides for positioning adjustments in the x-y plane 16 and about the z axis. The z axis (FIG. 18) extends axially along the upright member 20. The portion of the device that mounts first support 20 to base 10 is to the left of wall 17 (FIG. 1) of base 10. It comprises brace means 24 and 25, each having a horizontal slot 26 and 27 (FIG. 1, 3–5), which receives the ends of stand member 28 (FIGS.

2-5). Stand 28 has a central slot. The ends of stand 28 are slidable in slots 26 and 27. Set screws 53 and 54 (FIG. 2) fix stand 28 within slots 26 and 27. These adjustments provide gross movement of vertical support member 20 about the z axis.

Fine adjustment is also provided. Flange 30 of pin 31 (FIG. 5) rests on stand 28 and in circular recess 33 of intermediate member 34. Pin 31 extends upward through central opening 36 of pedestal 37 and into a wider base 39 of vertical support member 20. Base 39 and pedestal 37 are fixed to pin 31 by adhesive or other means, and pin 31 is permitted to rotate relative to stand 28 and intermediate member 34 because of the mounting. Teflon pads or other friction reducing surfaces may be provided. Protractor 41 with scale 42 (FIGS. 2 and 5) may also be provided between base 39 and pedestal 37. The bottom of pin 31 is attached to under support 32 directly below stand 28. Under support 32 pivots relative to stand 28.

Figure 2:
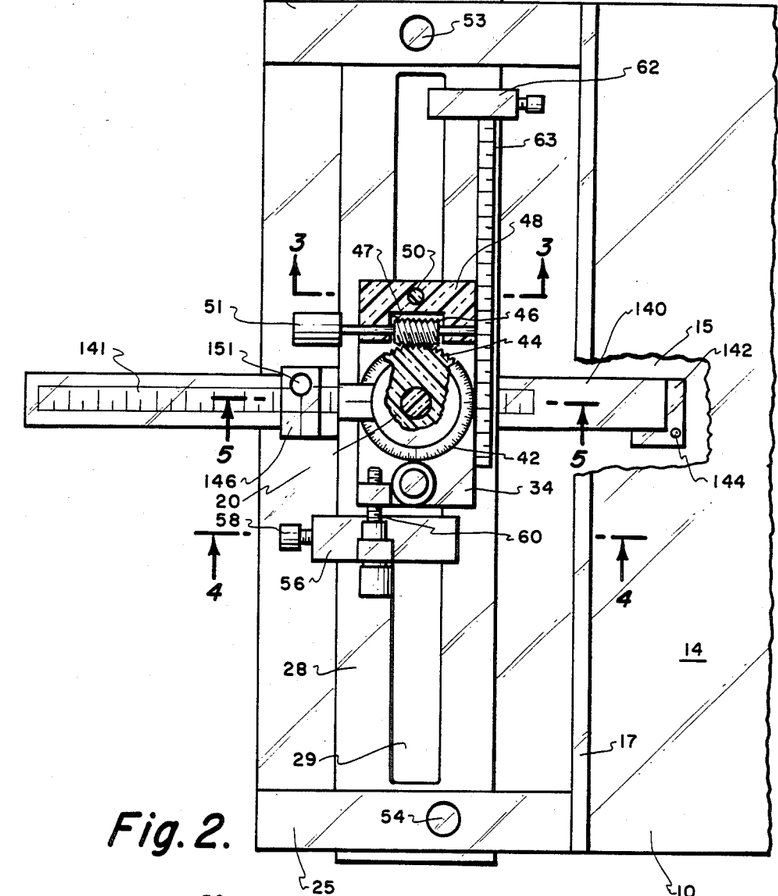
FIG. 2 (sheet 2) is a plan view, partially in section, of the probe guide of the present invention taken through plane 2—2 of FIG. 1.
Figures 3, 4:
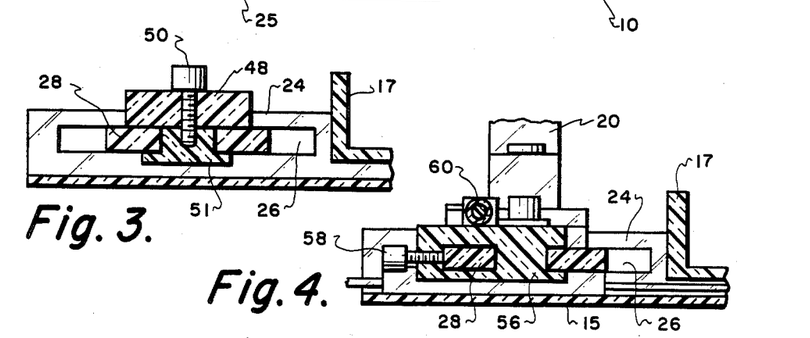
FIGS. 3 and 4 (sheet 2) and FIG. 5 (sheet 3) are all sectional views of details of the guide of the present invention taken respectively through planes 3—3, 4—4 and 5—5 of FIG. 2.

The outside of pedestal 37 is toothed as at 44 (FIG. 2). Worm gear 46 is mounted within recess 47 of block 48 (FIGS. 2 and 3). Nut 49 and bolt 50 (FIG. 3) hold block 48 to stand 28. Worm gear 46 is turned by handle 51, and the worm gear engages teeth 44 causing pedestal 37, pin 31, under support 32 and first support member 20 to rotate. Rotation is demonstrated schematically by the arrow extending around the z axis in FIG. 19.

When set screws 53 and 54 are unlocked, stand 28 can also slide in the x or y directions (FIG. 19) for gross positioning along the x axis and some degree along the y axis. There is also a system for fine positioning these adjustments. As shown in FIG. 2 and 4, a small block 56 is slidably mounted on stand 28, and set screw 58 extends through block 56 and can be in contact with stand 28. An adjustment screw 60, which rotates in block 56 connects the block with intermediate member 34 (FIG. 2). When set screws 58 is loosened, block 56 and intermediate member 34 can slide together along the x axis on stand 28. Locking set screw 58 fixes the position of block 56. Small movements of intermediate member 34 are then possible by using adjustment screw 60. Normally this fine adjustment is made in conjunction with x-ray target locating, which is explained below.

Another sliding member 62 may be mounted on stand 28 (FIG. 2) for a variety of purposes, such as saving a position determined during previous measuring. It may also be useful to mount a scale 63 along the x axis on stand 28.

The remaining structure shown in FIGS. 2 and 5 primarily relate to structure that aligns the system in conjunction with the x-ray fluoroscope and is described later.

Figure 6:
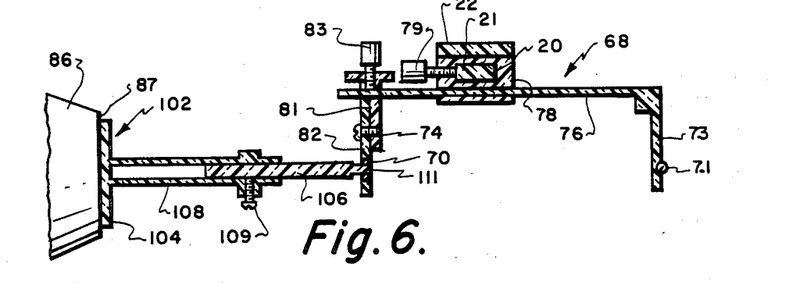
FIGS. 6 and 7 (sheet 3) are both sectional views of the present invention taken respectively through planes 6—6 and 7—7 of FIG. 1.

The present invention also includes first and second target sighting means attached to the first support member. The first target sighting means is best shown in FIGS. 1 and 6 in the exemplary embodiment. The first target sighting means 68 comprises two target markers, ring 70 and ball 71, mounted on extensions 73 and 74 on arm 76. Extension 74 is formed of two small plates 81 and 82 attached together, and plate 81 is held on arm 76 by attaching screw 83 (FIG. 6). Arm 76 is attached to block 78, which can slide up and down along front vertical post 21 and between post 21 and rear vertical post 22 of vertical support member 20 (FIG. 6). Set screw 79 fixes the position of block 78, and thus the remainder of the first target sighting means vertically on first support member 20 (FIG. 1).

FIG. 1 shows an x-ray fluoroscope which includes x-ray projector 86 and receiver 88. For accurate measurements, the axis of projection from projector 86 to receiver 88 must be parallel with top surface 14 of base 10 (thus parallel to reference plane 16, the x-y plane). Conventional levels could be used. The present invention uses a pair of target markers 70 and 71 on arm 76, which are perpendicular to vertical support member 20, and therefore, parallel to first reference plane 16. If the x-ray image shows ball 71 in ring 70, the line from the x-ray through the target markers is perpendicular to upright support 20.

Alignment with target 6 takes place as follows. First, there must be a center to x-ray receiver 88 is centered. This can be accomplished in several ways.

Figure 15:
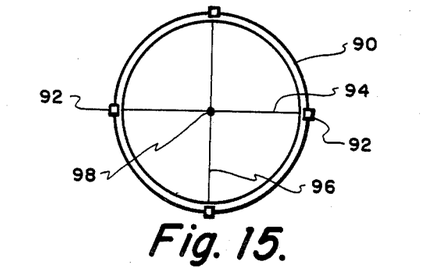
FIG. 15 (sheet 6) is an end view of a subassembly attached to the fluoroscope receptor used in the present invention.

A circular ring unit 90 (FIGS. 1 and 15) may be clamped onto the front of x-ray receiver 88. Ring unit 96 has several flexible clamps 92 that slide onto and hold the outside of x-ray receiver 88. Although not shown, the outside of x-ray receiver 88 could have a circumferential slot that engages a portion of flexible clamps 92 and permits ring unit 90 to rotate. Ring unit 96 also has two cross-hairs 94 and 96 (FIG. 15), which are perpendicular to each other and are both opaque to x-rays. An opaque, small disk 98 is mounted at the intersection of cross-hairs 94 and 96.

Figure 16:
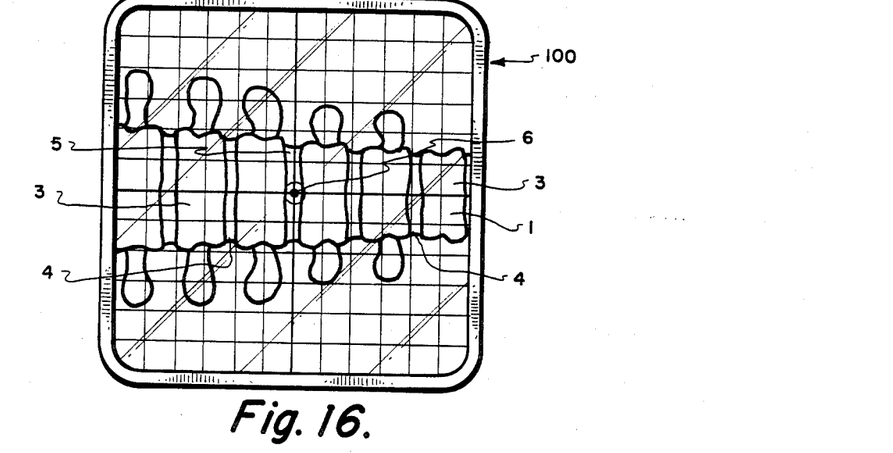
FIG. 16 (sheet 6) is a view of an x-ray viewing screen showing the x-ray image of the spine when the fluoroscope is projecting generally horizontally through the spine.
Figure 17:
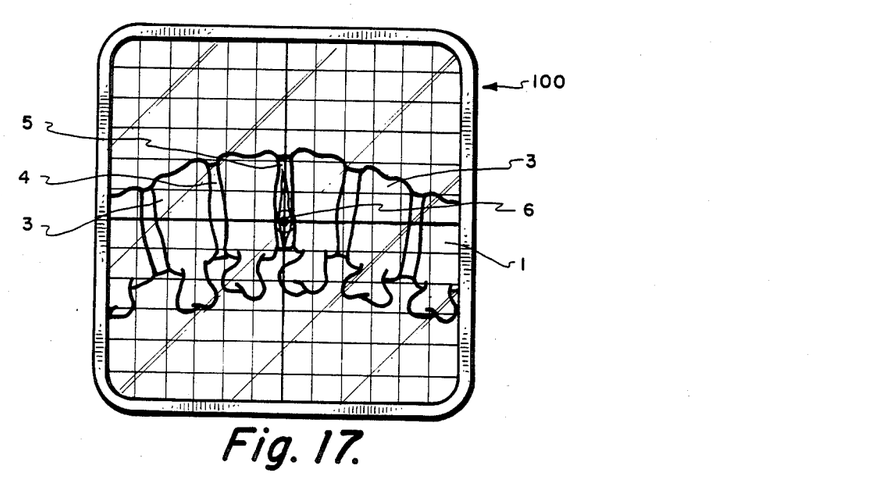
FIG. 17 (sheet 6) is a view of the screen showing the x-ray image of the spine when the fluoroscope is projecting vertically through the spine.

When x-ray receiver 88 and projector 86 are properly aligned, the image of ball 71 should be within the image of ring 70, and they should each be aligned with the center of receiver 88 at the image of disk 98 between cross-hairs 94 and 96. In lieu of the cross-hairs just discussed, the center could be marked on x-ray screen 100, or one can use the scale on the screen (FIGS. 16 and 17). Both the x-ray unit 86 and 88 and first target means 68 can move vertically for determining this alignment. Instead of vertical adjustment of the x-ray unit, surgical table 12 can move up or down.

In addition or as an alternative, an alignment member can be added to the front face of x-ray projector 86. X-ray alignment member 102 has a base 104 and an elongated pointer member 106 that is received and telescopes into and out of tube 108, which is perpendicular to base 102. Because the front face 87 of x-ray projector 86 is perpendicular to the axis of projection of the x-rays, because base 104 is parallel to face 87 and because pointer 106 is perpendicular and centrally located on base 104, pointer 106 is at the center of the axis of projection of the x-rays emanating from projector 86. Front end 111 is sized to fit within ring 70 (FIGS. 6). One can therefore use x-ray aligning member 102 to position the x-ray projector 86 and first x-ray target means 68 relative to each other.

At this point, the position of the actual target, in this case the treatment sight on the disk space, has not been discussed. This location, however, will appear on the fluoroscope screen, and the view of the spine 1 of patient 2 is shown in FIGS. 16 and 17. FIGS. 16, being the view taken horizontally through the patient with the fluoroscope positioned as in FIG. 1 shows six vertebrae 3 with connecting disks 4 between them. It is presumed that disk 5 at the center of screen 100 is the damaged disk.

Upright support 20 and the fluoroscope are moved horizontally along the x axis (FIG. 19) until the image of ball 71 within ring 70 is at target 6 or directly above or below the target on screen 100. The screen grid or the image of crosshairs 96 and 94 assist this measurement. The gross and fine positioning was discussed earlier. This sets the position of the x-y plane.

Next, the vertical position of target 6 on the z axis is determined. First target means 68 either and the x-ray fluoroscope or the surgical table 12 are moved up or down until the image in screen 100 of ball 71 is within ring 70 and is at target 6, the treatment point. Set screw 79 (FIG. 6) is the locked, which fixes the vertical position of first x-ray blocking means 68. That position is then noted. At this point, the position of the target area or treatment sight along the x axis is determined by gross and fine positioning vertical support member 20.

The next step measures the distance from the z axis to target 6 along the y axis. Second target sighting means, generally 116 (FIGS. 1, 6 and 7), includes an arm 118 (FIGS. 7 and 8), which extends at a right angle to upright support member 20 above patient 2. Upper arm 118 has an attaching portion 120 (left side of FIG. 1) for attaching to the upright support member 20. Essentially, portion 120 has an opening 121 through which front support member 21 extends. Another region 119 fits in slot 23 between main support 21 and rear support 22 (FIGS. 7). Arm 118, therefore can move up and down along upright support member 20. Set screw 123 extending through attaching portion 120 contacts front support member 121 to fix the position of arm 118. The vertical position of the arm is not crucial. It must be out of the way of patient 2 (FIG. 1) and should be somewhat close to him.

Arm 118 has a rear wall 124, a front wall 126 and a slot 125 between the rear and front wall. Front wall 126 has a measuring scale 127, the purpose of which is discussed below.

Sight member 128 has an upstanding portion 129 (FIGS. 7 and 8), which extends into slot 125 of arm 118 and permits upper sight member 128 to move along the slot. A set screw 131 (FIG. 8) fixes the position of upper sight member 128 along arm 118. Horizontal portion 130 of upper sight 128 is designed to be horizontal, that is, parallel with upper surface 14 of base 10 (FIG. 1) x-y reference plane 16 (FIG. 19). Upper sight 128 has a small metal ring 136 and three metal wires 133, 134 and 135. Wires 133 and 134 are designed to be parallel with arm 118, and wire 135 is perpendicular to the other two wires and to the arm, and all of the wires are aligned with metal ring 136 (FIG. 7). The x-ray fluoroscope 86, 88 is designed to project x-rays through upper sight 128, and the images of the metal wires and ring will be visible in the x-ray screen because they are metal and opaque to x-ray. A second x-ray target sighting means 116 could be similar in design to the first x-ray sighting means 68. That is, ring 70 and ball 71 are mounted on two spaced apart arms 73 and 74, but the distance apart of these two arms is relatively small. A shorter distance can lead to small errors. These errors, however, should not be too great because the first target sighting means 68 is relatively close to target 6 as best seen in FIG. 1. Also, there is no structure of the present device on the other side of patient 2. Upper arm 118, however, is farther from the treatment target 6 (FIG. 1), and there is structure of the device on the other side of patient from arm 118. Therefore, the exemplary embodiment separates the sites of the second target sighting means.

Figure 5:
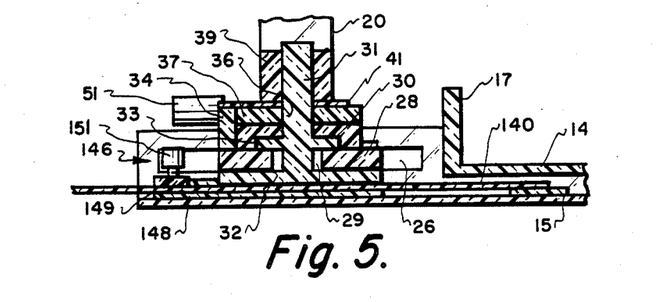

Second target sighting means also includes a bottom arm 140 (FIG. 1, 2 and 5). Arm 140 is also perpendicular to upright support member 20, and it is designed to be parallel with upper arm 118. Bottom arm 140 has a lower sight member 142 with a ball or small disk 144 positioned on the lower sight. The horizontal distance along the x axis (FIG. 19) of both ring 136 and disk 144 is equal so that both can be used for aligning. In theory, both could be tied together so that movement of one would move the other, and they would both move the same distance along the y axis. The exemplary embodiment operates differently, however. Bottom arm 140 extends into a pinching member 146 attached to the bottom of under support 32. Pincher 146 pivots as pedestal 37 and upright support 20 pivot. Pincher 146 has a bottom wall 148 and a top wall 149, and Lower arm 140 extends between the lower wall 148 and upper wall 149 of the pincher (FIG. 5). Screw 151 adjusts the tension between the lower and upper walls of the pincher, but the tension is normally kept at such a degree that some left-right movement (FIG. 5) is permitted.

For measuring the y coordinate, the x-ray fluoroscope is swung 90° so that projector 86 is projecting x-rays vertically downward through upper sight 128 and target 6. The first measurement is a tentative one unless it can be assured that projector 86 is actually projecting perpendicular to horizontal reference surface 16 and thus parallel to upstanding support 20. One could use a plumb or spirit level for this purpose. The surgeon viewing screen 100 sees the view shown in FIG. 17. To assure that all is aligned, however, the position of upper sight 128 along scale 127 (FIG. 1) is noted. Scale 127 reads from left to right (FIG. 1), with the zero mark corresponding to the z axis.

Lower arm 140 also has a scale, and the lower arm is moved to a distance corresponding to the distance read from the scale on the upper arm. Scale 141 (FIG. 2) reads from right to left, and it is offset a small distance because a portion of it is covered by stand 28. If the distance of ring 135 on upper sight 128 from the z axis (upright arm 20) is the same distance of disk 144 on lower arm 140 from the z axis, and if the x-ray image of the ring and disk are through target 6, the system is aligned as is ready for use.

It should be noted that the target would be reached by proceeding along the lines created by a first or the second target sighting means. For example, if one wanted to reach target 6 horizontally, one could use a tool and proceed horizontally along the line created by the first target sighting means, and the probe, drill, needle or other entry device would proceed from the z axis the exact distance measured along the y axis equal to the distance of one of the second target sighting means 116 from the z axis. Similar entry could be made along the line created by the second target sighting means. For work in chemonucleolysis on most vertebrea, it is necessary to approach the disk spaces at a 45° angle because of the geometry of the vertebrea. Other surgical or non-surgical procedures may require entry at a different angle.

The present invention, therefore, includes a probe support positioned along the first support member at a predetermined angle to the first support. In the exemplary embodiment, probe support 154 (FIGS. 1, 9 and 10) is mounted for vertical movement on upright support 20. Probe support 154 includes a connecting portion 156 (FIGS. 9 and 10) that includes an opening 157, which receives front upright support 21. Wall 159 extends between rear upright support 22 and main support 21, and connecting portion 156 and the entire probe support 154 moves vertically on upright support 20 (FIG. 1). Set screw 161 fixes the vertical position of probe support 154.

Figure 9:
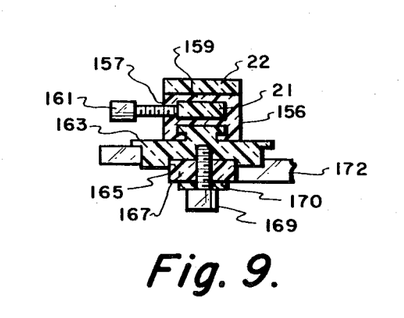
FIG. 9 (sheet 4) is a sectional view through plane 9—9 of FIG. 1 and shows some of the details of the mechanism for adjusting the angle of the probe support.
Figure 10:
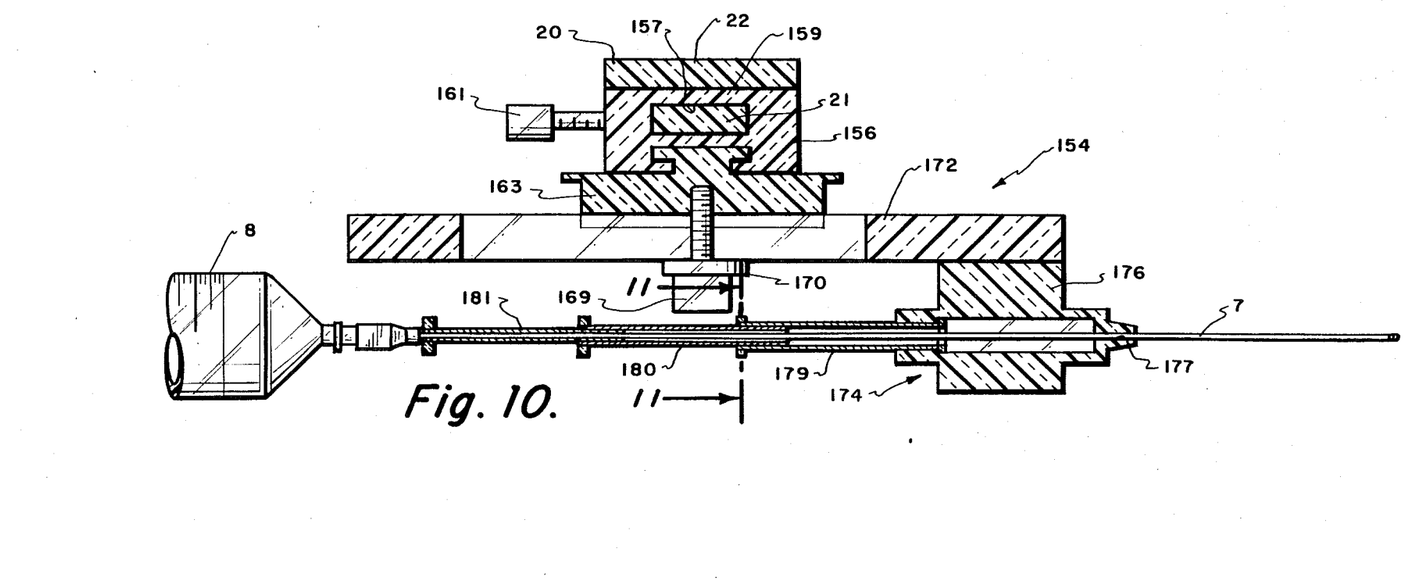
FIG. 10 (sheet 4) is a sectional view primarily of the probe support and the first support of the present invention and is taken through plane 10-1 in FIG. 1.
Figure 11:
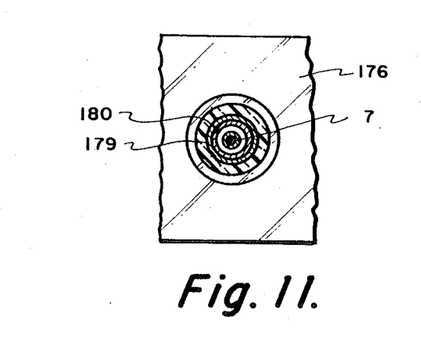
FIG. 11 (FIG. 4) is a sectional view showing some of the details of the probe support, and is taken through plane 11—11 in FIG. 10.

Intermediate member 163 is fixed to connecting member 156 (FIGS. 9 and 10). Recess 165 of intermediate 163 receives gear 167. A fastener such as screw 169, which extends through gear 167 into intermediate member 163 permits the gear to rotate in the recess. Washer 170 assists in the rotation (FIGS. 1, 9 and 10).

Probe arm 172 is attached to gear 167. The right end (FIG. 10) of probe arm 172 has a probe guider 174 (FIGS. 1 and 10). In the exemplary embodiment, probe guider 174 has a base section 176 with a lower channel 177, which has an inside diameter corresponding to the outside diameter of the needle, probe, drill or other object, needle 7 in the exemplary embodiment, that is to reach the target. The needle is connected to a hypodermic syringe 8 (FIGS. 1 and 10). Base section 176 also has three telescoping tubes 179, 180 and 181 (FIG. 10). The inside diameter of tube 181 is also approximately equal to the outside diameter of probe 7. Probe guider 174 is moveable to a predetermined angle relative to upright support 20 as probe arm 172 rotates about horizontal axis 190, an axis on the z axis parallel to the x axis (FIG. 19).

Worm gear 183 is mounted in an opening 184 of a lower portion of connecting member 156 (FIG. 1). Worm 183 engages teeth 185 on the outside of gear 167, and rotating handle 186 rotates worm 183 and causes gear 167 to rotate about axis 190. The angle of rotation of gear 167 can be read from scale 188 (FIG. 1).

At this point, one knows the vertical position (along the z axis) of target 6, the horizontal position $y_o$ (FIG. 18), and the predetermined angle a that is chosen for the probe to reach the target. For a given angle a, the vertical $z_o$ position of axis of rotation 90 (FIG. 8) of probe support 154 to intercept target 6 is:

$$z_o = y_o / \tan a)$$

Assuming as with the chemonucleolysis process that the probe should enter at 45°, the computation of the $z_o$ position is done as follows. One first reads the horizontal distance $y_o$ from scale 127 on horizontal arm 118. Angle a=45°. Tan 45°=1. Therefore, $z_o = y_o$.

To facilitate adjustment measurement, scale 138 on main upright support 121 can slide vertically. FIG. 7 shows a possible arrangement that provides for vertical movement of scale 138 along main upright support 21. The scale is fixed to first target sighting means 68 and moves up and down with it and the zero mark is aligned with the axis extending through ring 70 and ball 71 offset a distance equal to a convenient scale reading mark on probe support 154 above axis of rotation 90. The read distance when the probe support is at 45° should be equal to the horizontal distance read from scale 127 on arm 118.

The surgeon can now move syringe 8 to push probe 7 through the skin of patient 2 toward target 6 in disk space 5. The surgeon follows the image of probe 7 on x-ray screen 100. Its image should correspond to the centre vertical line on screen 100 that passes through target 6. In many instances, one follows the path of the bottom end of the probe to see that its image reaches target 5. Distance measuring is also possible with the present invention. The distance w along target line of sight 92 from pivot 90 to target 6 is as follows:

$$W = z_o / \cos a = z_o (\sec a)$$

A scale can be provided on probe arm 172 to read the distance which syringe 8 is moved to the right (FIG. 10). If probe arm 172 can be expanded to account for the correct trigonometry function of the predetermined angle chosen.

Figures 12, 13, 14:
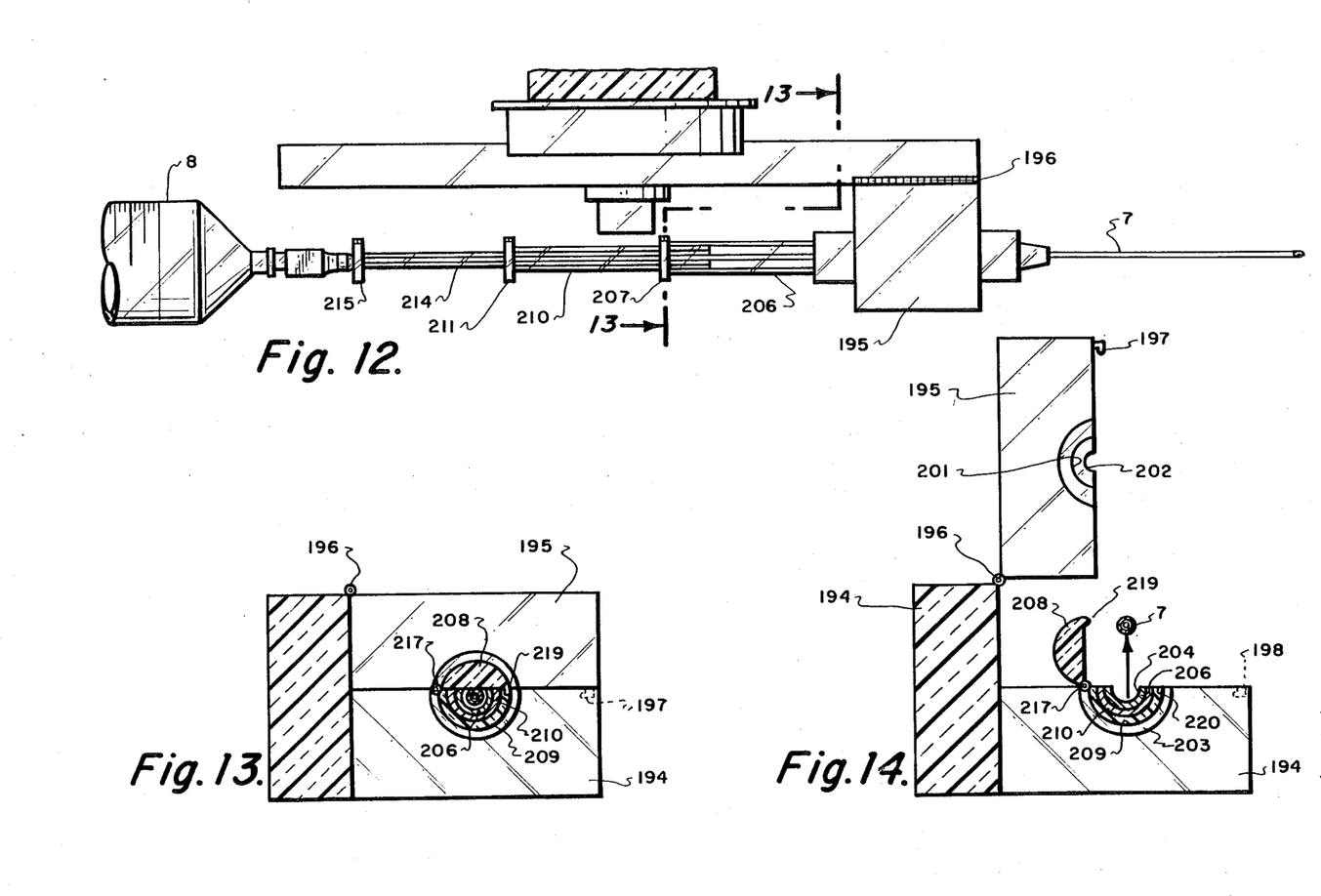
FIGS. 12, 13 and 14 (FIG. 5) are sectional views showing details of a modification of the probe support of the present invention.

In some instances, it may be desirable to insert probe 7 into the skin and then have it removeable from the probe guide of the present invention. A system for accomplishing this is shown in FIGS. 12, 13 and 14. What had been base section 176 in the first embodiment FIG. 10 now includes base section 194 with a cover 195 hinged at 196. A small latch member 197 (FIG. 14) may extend into a mating detend 198 to lock cover 195 to base portion 194. Both cover 195 and base section 194 have somewhat large diameter semi-circular recesses 201 and 203, which receive telescoping members 206, 210 and 214. Smaller diameter recesses 202 and 204 receive the probe and act as a probe guider. Each of the telescoping portions 206, 210 and 214 also open so that when cover 195 opens, probe 7 can be removed. The telescoping members each have a pair of locking flanges 207, 211 and 215. Flange shown in FIGS. 13 and 14 and comprises an upper, semi-circular portion 108 and a lower half ring portion 209. A hinge 217 allows upper and lower members 208 and 209 to pivot relative to each other. Upper member 208 may have a tab 219 that is received within detent 220.

When the telescoping member and the base members are open (FIG. 14, probe 7 can be removed and any interfering parts on the guide member of the present invention can be moved out of the surgeon's way so that he or she will be able to move the probe freely.

The previous explanation of the operation of the device of the present invention assumed to some degree that the y axis extended perpendicular to upstanding wall 17 (FIGS. 1 and 2) especially because of the view shown in FIG. 2. As previously stated, upright support 20 may be mounted for rotation about the z axis, and a mechanism for adjustment has been described. FIG. 19 shows that the x and y axis have been rotated about the z axis through an angle b. This rotation, however, also rotates the rest of the parts of the guide of the present invention through the same angle, namely upper arm 118, lower arm 140, first target sighting means 68 and probe support 54. The fluoroscope then will also have to be aligned to account for the new angle.

In the chemonucleolysis method, an angled approach may necessary to reach the lower lumbar disk spaces because the iliac crest, the upper projection of the hip bone, blocks a straight approach.

In theory and as shown in FIG. 18, x-ray projector 86 can be mounted such that the line of projection is not at right angles. FIG. 18 shows a mid-position of x-ray projector 86 that directs x-rays along a different path. The geometry changes, but the calculations can be made relatively easily. This approach might be useful in situations where the vertical or horizontal readings cannot be made. Usually, the surgeon uses the angled projection merely to follow the path of the needle.

Various modifications and changes may be made in the configuration described above that come within the spirit of this invention. Much of the construction of the plastic parts of the embodiment are designed for machine shop manufacture and assembly of few units. In production, two or more parts may be combined into a single molded part. Features may be replaced. The invention embraces all such changes and modifications coming within the scope of the appended claims.

We claim:

1. A guide for locating a target object within a visually opaque but X-ray transparent object comprising:
   a. base means for creating a first reference plane positionable under the opaque object;
   b. a first support member attached to the base and extending perpendicular to the first reference plane;
   c. a first and second target sighting means attached to the first support member; each target sighting means having a portion opaque to X-ray first target mounting means on the first target sighting means for attaching the first target sighting means to the first support member for movement along the first support member such that the opaque portion of the first target sighting means, the axis of the projection of an X-ray generator and receiver and the target object are in a first reference line that is parallel to the first reference plane; the second sighting means being positionable relative to the first support member such that the opaque portion of the second target sighting means, and the axis of projection of the X-ray generator and receiver and the target object are in a second reference line, which is perpendicular to the first reference plane;
   d. a probe support positionable along the first support member at a predetermined angle to the first support member at a distance above the first reference line equal to the distance from the first support member to the second reference line divided by the tangent of the predetermined angle.

2. The guide of claim 1 wherein each target sighting means comprises a pair of target markers.

3. The guide of claim 1 wherein the second target sighting means comprises an arm mounted perpendicular to the first support member and including an upper sight member moveable along the arm, the opaque portion of the second target sighting means being on the upper sight member.

4. The guide of claim 3 further comprising a second arm and means for mounting a second arm on the other side of the target from the first arm and extending perpendicular from the first support member, the means for mounting the second arm permitting the second arm to move along the line perpendicular to the first support member.

5. The guide of claim 1 further comprising connecting means between the first support member and the base means for rotating the first upright support about an axis perpendicular to the base means.

6. The guide of claim 5, the connecting means further comprising means for allowing movement of the first support member along the base.

7. The guide of claim 6 further comprising attaching means between the probe support and the first support member for adjusting the predetermined angle.

8. The guide of claim 7 wherein the attaching means includes a connecting portion moveable along the first support, a gear totating on the connecting portion, a probe arm on the gear and rotating with rotation of the gear and guider means on the probe arm for receiving a probe and permitting the probe to move toward and away from the target.

9. The guide of claim 8 further comprising opening means on the guider means for permitting the probe to be removed from the guider means.

10. A method for guiding an instrument to a target object located within a visually opaque but X-ray transparent object comprising:
   a. creating a first reference plane under the opaque object;
   b. mounting an upright support in an upright line perpendicular to the first reference plane;
   c. aligning the transmitter and receiver of an X-ray fluoroscope in a plane including the target object, the plane being parallel to the first reference plane;
   d. moving a first target sight, having a part opaque to x-ray, along the upright support to a position such that the part of the first target sight is aligned with the transmitter, receiver and target object, thereby creating a first X-ray imaging plane;
   e. rotating the X-ray transmitter and receiver to a second X-ray imaging plane including the target object that is perpendicular to the first X-ray imaging plane;
   f. moving a second target sight, having a portion opaque to x-ray, perpendicular to the upright support to a position such that the portion of the second target sight is aligned with the target object and the second X-ray imaging plane; and
   g. positioning the instrument at an angle to the first reference plane at a vertical position above the first X-ray imaging plane equal to the distance from the upright support to the second X-ray imaging plane divided by the tangent of the angle that the instrument makes to the first reference plane.

* * * * *